United States Patent [19]
Parins et al.

[11] Patent Number: 5,540,685
[45] Date of Patent: Jul. 30, 1996

[54] BIPOLAR ELECTRICAL SCISSORS WITH METAL CUTTING EDGES AND SHEARING SURFACES

[75] Inventors: David J. Parins, Corcoran; Richard K. Poppe, Minneapolis, both of Minn.

[73] Assignee: Everest Medical Corporation, Minneapolis, Minn.

[21] Appl. No.: 435,305

[22] Filed: May 5, 1995

Related U.S. Application Data

[63] Continuation-in-part of Ser. No. 369,379, Jan. 6, 1995, abandoned.

[51] Int. Cl.⁶ .................................................. A61B 17/39
[52] U.S. Cl. .............................. 606/51; 606/48; 606/50
[58] Field of Search .................................. 606/48, 50, 51

[56] References Cited

U.S. PATENT DOCUMENTS 5,324,289  6/1994  Eggers ............................. 606/48
5,352,222  10/1994  Rydell .
5,356,408  10/1994  Rydell ............................. 606/48

FOREIGN PATENT DOCUMENTS 0518230  12/1992  European Pat. Off. ............ 606/48
0624348  11/1994  European Pat. Off. ............ 606/51

*Primary Examiner*—Lee S. Cohen
*Attorney, Agent, or Firm*—Haugen and Nikolai, P.A.

[57] ABSTRACT

A bipolar electrosurgical scissors for use in open or endoscopic surgery has a pair of opposed metal blade members pivotally joined to one another and to the distal end of the scissors itself by a rivet. Each of the blade members comprises a cutting blade having an electrode on the non-shearing surface. An intermediate insulative coating is disposed between each cutting blade and its associated electrode coating. The cutting blade is preferably fabricated from metal such as stainless steel and the electrode coating comprises metal traces deposited thereon through a mask to yield a desired pattern extending along but separated from the blade's cutting edge. Cutting is performed, steel-on-steel, without causing a short circuit between the blades which themselves may function as one of the bipolar electrodes.

12 Claims, 5 Drawing Sheets

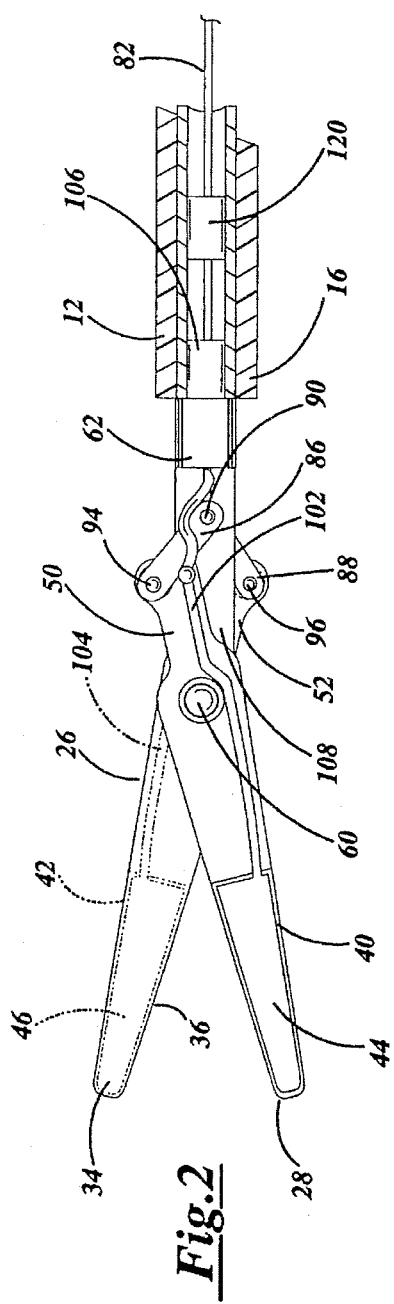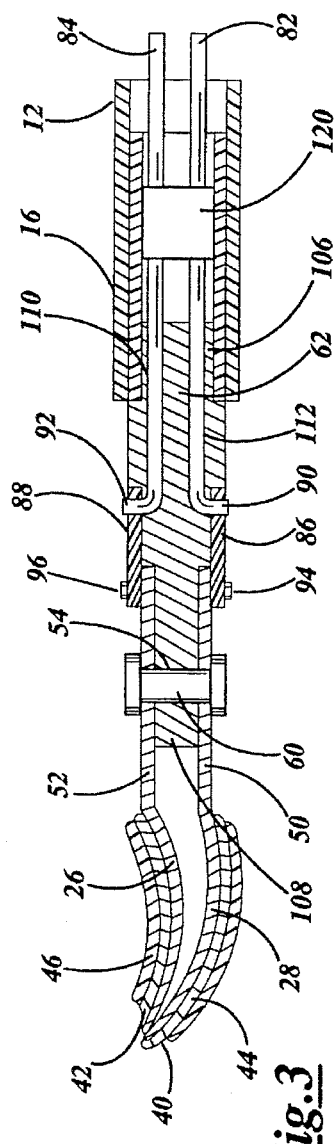

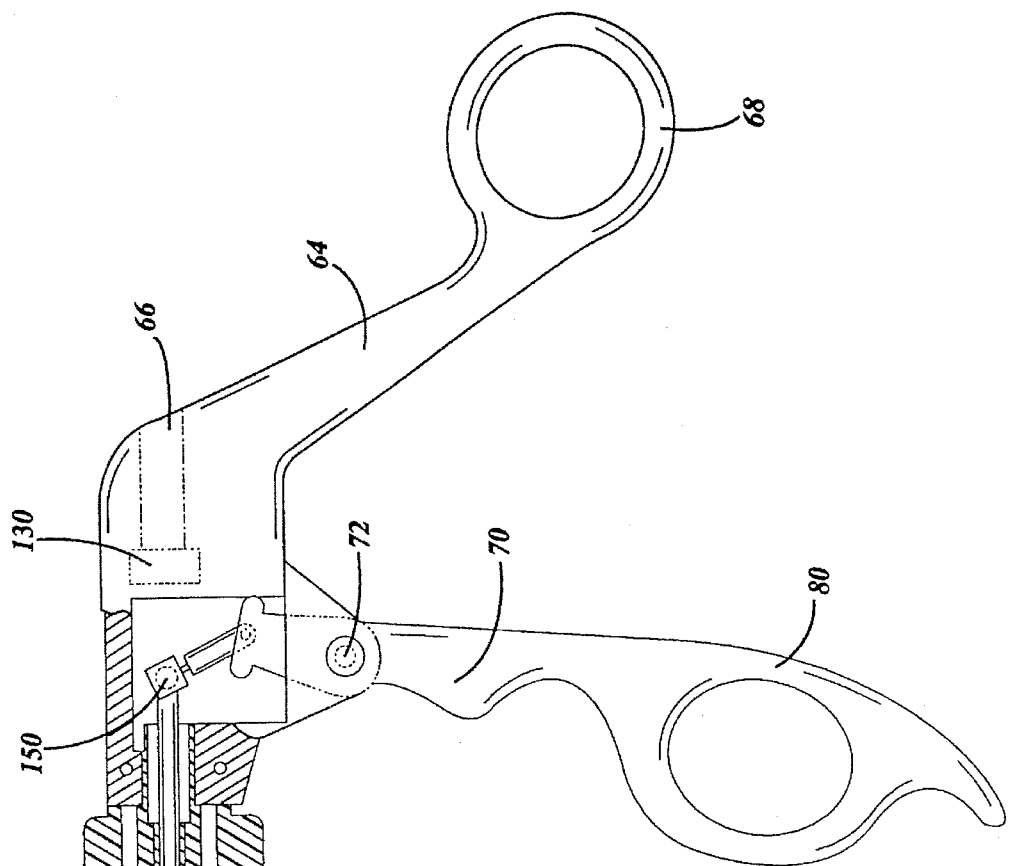
Fig.6
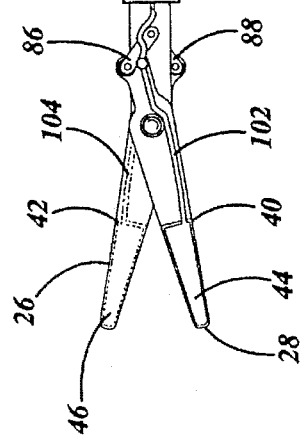
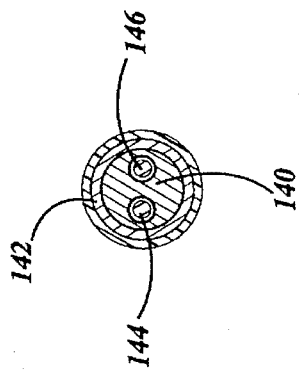
Fig.7

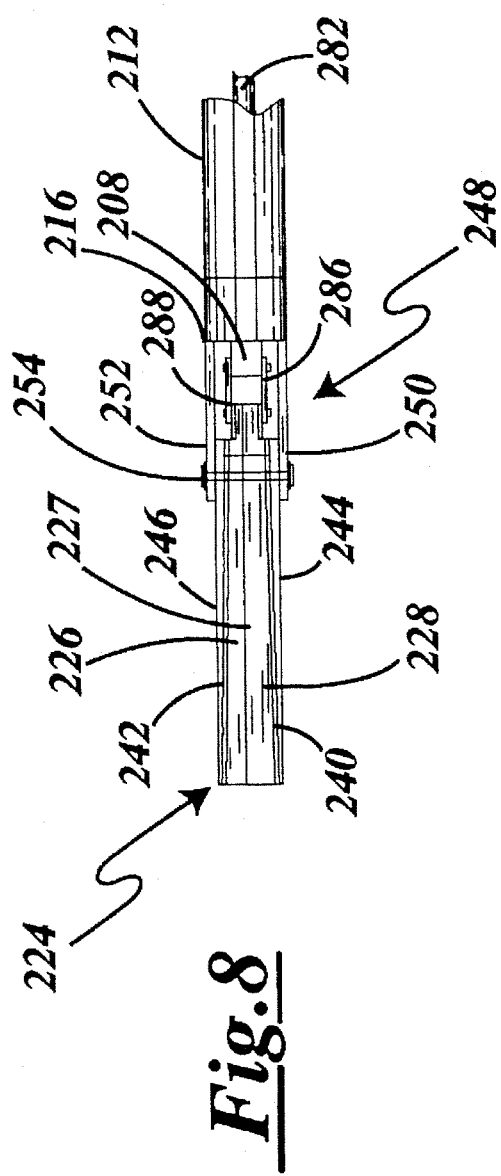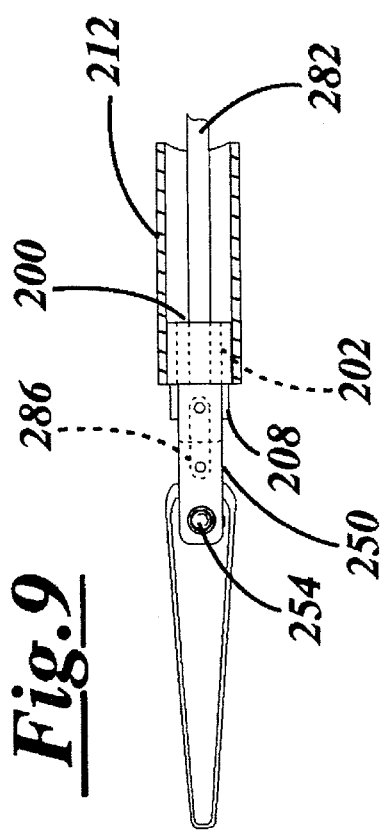

BIPOLAR ELECTRICAL SCISSORS WITH METAL CUTTING EDGES AND SHEARING SURFACES

CROSS-REFERENCE TO RELATED APPLICATION

The present application is a Continuation-In-Part of my application Ser. No. 08/369,379, filed on Jan. 6, 1995, and entitled "BIPOLAR ELECTROSURGICAL SCISSORS WITH METAL CUTTING EDGES AND SHEARING SURFACES", now abandoned.

BACKGROUND OF THE INVENTION

1. Field of the Invention

This invention relates generally to the design of a bipolar electrosurgical scissors, and more particularly to a surgical scissors incorporating bipolar electrodes on its blade elements, such that mechanical cutting with subsequent electrocoagulation can be achieved without requiring an instrument exchange.

2. Discussion of the Prior Art

Electrosurgical devices are well-known surgical instruments used in coagulating and cutting procedures. Electrocoagulating instruments include at least one conductive electrode. Radio frequency energy is conducted through this electrode to either a remote conductive body-plate (monopolar) or to a second, closely-spaced conductive electrode (bipolar). Current passing through the gap between the two electrodes will coagulate blood and other body fluids placed between the two electrodes.

Monopolar electrocautery instruments suffer from the fact that the return path between the active electrode and the large area body-plate can be unpredictable as the electrical current seeks the return electrode through the path of least resistance. With bipolar electrosurgical instruments, however, because the two electrodes are closely spaced to one another, usually at the distal end of an instrument handle, the return path is very short and involves the tissue and fluids in the short path between the electrodes. Although there is available in the prior art monopolar scissors where both of the scissors blades form one conductive pole and with a remote body plate being the second pole, such a scissors still has the drawbacks of being a monopolar device.

The prior art also contains a scissors-type instrument for mechanically snipping tissue during the course of an endoscopic procedure. Such a scissors comprises a pair of blades fabricated from metal and disposed at the distal end of an elongated tubular member whose outside diameter is sufficiently small to allow it to be passed through the working lumen of an endoscope, a laparoscope or other similar devices known in the art. Disposed at the proximal end of the rigid tube is a scissors-type handle having a pair of members pivotally coupled to one another, each with a finger-receiving loop. An appropriate mechanical coupling is made between the handle members and the blades so that manipulation of the handle members will result in an opening and closing of the blades relative to one another. When using a mechanical cutting scissors of this type to excise tissue, bleeding results when a blood vessel is cut. At that point, it is generally necessary for the surgeon to remove the scissors instrument from the working lumen of the endoscope and then insert an electrocoagulator down the endoscope to the site of the bleeder. This instrument exchange is time-consuming and in a surgical procedure where moments count, it would be desirable to have a scissors-type instrument for cutting but which also incorporates the ability to coagulate blood and other body tissues using RF energy.

With metal-to-metal contact along the sharpened edges of the two blades, an electrical short results if the two blades act as separate electrodes of a bipolar pair. Furthermore, the attempt to use a metal rivet or screw as the pivot point for the blades is another area where short-circuiting is likely to occur. When such a short exists, the electrical current does not flow through the blood or body tissue to effect coagulation, but instead, follows the short-circuit path from one electrode to the other. This has been addressed in the prior art by a scissors with conductive metal blade supports to which sharpened metal cutting blades are affixed using a nonconductive epoxy bonding and spacing layer. In this regard, reference is made to the Rydell U.S. Pat. No. 5,352,222 assigned to the assignee of the present invention. The manufacture of such a scissors involves the somewhat time consuming process of bonding the cutting blades to the metal blade supports.

Another prior art scissors, disclosed in the Rydell U.S. Pat. No. 5,356,408, assigned to the assignee of the present invention, incorporates honed ceramic cutting and shearing surfaces on the opposed interior surfaces of metal blade support members. The blade support members are wired to act as electrodes. However, ceramic is a fragile, brittle material and the grinding operations for ceramic can be expensive. Furthermore, the ceramic surfaces must be affixed to the metal blade members in a way that prevents delamination during use.

To date, however, there is not available in the marketplace a bipolar electrosurgical scissors having two metal blades pivotally joined to one another with an insulating layer applied to the non-shearing surfaces of the blades and with electrodes located on the insulating layer of the blades and which are, thus, electrically isolated from the metal cutting edges and shearing surfaces of the blades. A need therefore exists for a bipolar electrosurgical scissors for use in both open and endoscopic surgical procedures where the shearing surfaces may be surgical steel, but where the exterior surface portions of the metal blades can be coated or otherwise provided with an insulating layer on which conductive metal electrodes are disposed, allowing the scissors to be used in performing bipolar electrocoagulation as the cutting progresses.

SUMMARY OF THE INVENTION

It is accordingly a principal object of the present invention to provide a bipolar, electrocoagulating and cutting instrument having metal scissors blades for the mechanical cutting of tissue and for supporting electrodes thereon which may cooperate with the blade on which they reside as a second electrode or with one another to coagulate tissue and body fluids during the cutting act.

Another object of the present invention is to provide a bipolar scissors having a miniaturized distal blade configuration that allows the instrument to be inserted through a laparoscope, trocar, or the working lumen of an endoscope.

Still another object of the present invention is to provide a bipolar-type scissors instrument having metal, such as stainless steel, cutting blades and which utilizes a push rod and pivot combination to cause movement of one or both of the scissors blades through manipulation of a scissors-style handle mechanism at the proximal end of the instrument and wherein an electrode is supported on the non-shearing surface of each of the blades but is insulated therefrom, allowing the electrodes to be energized from an RF source to effect bipolar electrocoagulation of cut tissue.

The foregoing objects of the invention are achieved by providing an instrument having two metal blades, each with a shearing surface and a honed cutting edge. The metal blades are coated on their exterior, non-shearing surfaces with a non-conductive insulating layer. A conductive electrode is placed atop the insulating layer. In forming an endoscopic scissors, this blade assembly is secured to the distal end of an elongated tube. An actuating coupling extends through the tube to a movable portion of a scissors handle so that when the handle is manipulated, the blades can be made to open and close relative to one another in a scissors-like fashion. Also extending through the lumen from electrical terminals on the handle to the conductive electrodes are conductors which permit a voltage to be applied between the two conductive electrodes located on the exterior, non-shearing surfaces of the cutting blades. Because each blade has the sharpened edge and shearing surface insulated from the conductive electrodes, there will be no short circuit between the blade members when cutting and coagulation occurs.

In an alternative embodiment, the metal cutting blades and the conductive electrodes are electrically connected to a RF voltage source so that the cutting blades are held at the same potential and the two conductive electrodes are at a second potential. Hence, a voltage exists between each of the blades and the conductive electrodes which it supports, but not between the blades themselves. When made to engage tissue, a coagulating current flows from the two conductive electrodes to the blades supporting them, but since the blades themselves are at the same potential, no shorting takes place between the blades.

The conductive electrodes may comprise metal traces placed on the insulating layers using a deposition or screening process known in the art or may comprise preformed metal strips bonded to the insulating layers on the cutting blades.

DESCRIPTION OF THE DRAWINGS

The foregoing features, objects, and advantages of the invention will become apparent to those skilled in the art from the following detailed description of a preferred embodiment, especially when considered in conjunction with the accompanying drawings in which like numerals in the several views refer to corresponding parts.

FIG. 2 is an enlarged, partial side elevation view of the distal portion of the scissors of FIG. 1 with the drawing being longitudinally sectioned;

FIG. 3 is a top plan view of FIG. 2 with the drawing partially sectioned;

FIG. 6 is a side elevation and partially cross-sectioned view of the bipolar scissors in accordance with an alternative construction;

FIG. 7 is a cross-sectional view taken along line 7—7 in FIG. 6;

FIG. 8 is a top plan view of the distal end portion of a further alternative construction of a bipolar scissors; and FIG. 9 is a partially sectioned side elevation of the embodiment of FIG. 8.

DESCRIPTION OF THE PREFERRED EMBODIMENT

Figure 1:
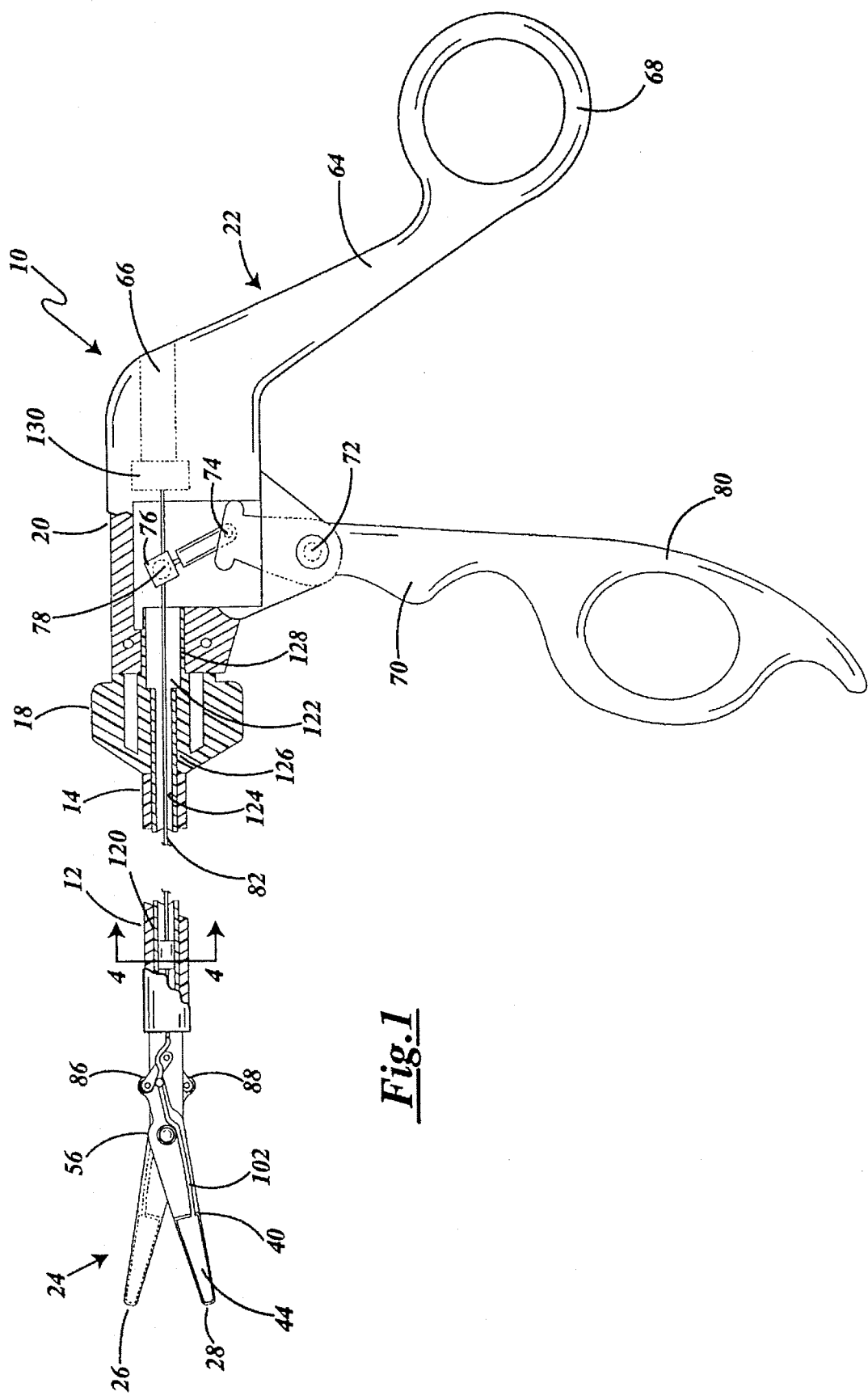
FIG. 1 is a side elevation view of one embodiment of a bipolar scissors device having two moveable blades, the drawing being partially sectioned to illustrate the working elements thereof.
Figure 4:
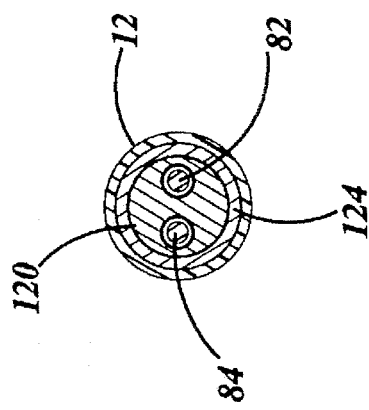
FIG. 4 is a cross-section view along line 4—4 of FIG. 1.

Referring to FIG. 1, there is indicated generally by numeral 10, a bipolar electrosurgical scissors for endoscopic surgery constructed in accordance with the present invention. It is seen to include an elongated tubular member 12 having a proximal end 14 and a distal end 16 with a lumen extending therebetween. The outer diameter (O.D.) of the tubular member 12 is sufficiently small to be passed through a trocar or the working lumen of an endoscope (laparoscope). Affixed to the proximal end 14 of the bipolar scissors 10 is a rotatable knob 18, appropriately mounted in the stationary portion 20 of a scissors handle assembly 22 so that the knob 18 can be rotated, the tubular member 12 turning with it. Affixed to the distal end of the tubular member 12 is a blade assembly 24, including blades 26 and 28.

Referring to FIGS. 2 and 3, there is shown a greatly enlarged side view of the distal end portion of the scissors and a horizontal cross-sectional view showing in greater detail the blade assembly 24. Blade 26 is seen to comprise a metal member, preferably fabricated from stainless steel, having an arcuate shearing surface 34 and a honed cutting edge 36. While the blade 26 is illustrated as having a arcuate profile when observed from the top as in FIG. 3, it can just as well be straight.

Each blade, 26 and 28, is provided with a non-conductive insulative layer 40 and 42, respectively on its exterior surface, i.e., the non-shearing surface. These coatings 40 and 42 are preferably 1–5 mils thick and can be a ceramic, glass, epoxy or another non-conductive material capable of withstanding high temperatures without limiting its dielectric properties. The insulative layers extend along the length of the cutting edges of the blades but are spaced away slightly therefrom. Conductive layers 44 and 46 are located on the insulative layers 40 and 42 of the respective cutting blades. The conductive layers 44 and 46 are preferably 1–5 mils thick and may comprise pre-formed stainless steel strips or, alternatively, metal traces which are paste deposited or vapor-deposited through a mask or selectively electroplated onto the non-conductive coatings and, as such, run parallel to the blades' cutting edges. These metal traces can be silver, gold, platinum, palladium, or other metal alloy suitable for use on medical instruments. As seen in FIGS. 2 and 3, the conductive layers 44 and 46 do not cover the entire non-conductive coated area. When the blades are in a closed position relative to one another, a gap between the two conductive layers is preferably in the range of 0.010–0.030 inches.

The proximal end portions 50 and 52 of the blades 26 and 28 each have a circular aperture extending therethrough for receiving a metal rivet 60 to pivotally secure the blades 26 and 28 to a hub member 62. The hub member 62 fits within the distal end 16 of the tubular member 12 and is appropriately bonded or swaged so as not to come loose.

The mechanism for actuating the blades 26 and 28 in a scissors-like motion is shown in FIGS. 1–5B. Disposed at the proximal end 14 of the tubular member 12 is the scissors handle assembly, indicated generally by numeral 22. The handle assembly 22 has a first (stationary) handle member 64 having first and second ends, with the first end thereof having a bore 66 extending therethrough. At its second end, the first handle member has a loop 68 intended to receive the thumb of an operator. The handle assembly 22 additionally has a second (movable) handle member 70 which is pivotable with respect to the first handle member 64 by virtue of being secured to the first handle member 64 with a pivot pin 72. The first end of the second handle member 70 has pivotally mounted thereto by pivot pin 74 an open top, u-shaped cradle member 76 shown in detail in FIGS. 5(a) and 5(b). Cradle member 76 supports a sphere 78 therein which is mechanically coupled to assembly 24. Situated at the second end of the second handle member 70 is a loop 80 to receive the forefinger of the operator.

The mechanism for opening and closing blades can incorporate one or two push rods connected to the cutting blades 26 and 28 with a linkage arrangement. With reference to the FIGS. 2 and 3, one embodiment is shown as having two rigid, electrically-conductive rods 82 and 84, each preferably covered with a layer of electrical insulation. The rods extend through the lumen of the tubular member 12. They are pivotally coupled to their respective blade members 26 and 28 by non-conductive rigid links 86 and 88. The distal ends of the rods 82 and 84 are turned laterally outwardly at 90 and 92 to fit through respective proximal pivot point openings 90 and 92 of the links 86 and 88 and are peened thereafter to form a rivet type connection. Situated at each of the proximal portions of the blade members 26 and 28 are laterally projecting posts 94 and 96 which pass through distal pivot openings in links 86 and 88 to likewise form rivet type connections. Thus, the rigid links 86 and 88 are free to pivot at each of their respective proximal and distal end portions. An insulated conductive wire extends from each electrically conductive push rod 82 and 84 to the conductive coatings on their respective blade members 26 and 28.

As discussed earlier, the blade assembly 24 comprises, in addition to the blade members 26 and 28, a hub 62 (FIG. 2) having a proximal portion 106 and a distal portion 108. The distal portion 108 has a bore therethrough which provides a means by which the blade members are pivotally attached thereto via the rivet or screw 60. The proximal portion 106 of the hub 62 is pressed fit or screwed within the tubular member 12 and, as seen in FIG. 3, has two parallel longitudinal bores 110 and 112 through which the rods 82 and 84 pass. The hub 62 is preferably formed from a suitable ceramic, such as zirconia.

Proximal to the hub 62 within the tubular member 12 is disposed an insulating guide 120 through which the rods 82 and 84 pass. This insulator member 120 functions to electrically isolate the rods 82 and 84 from each other while mechanically acting to maintain them in parallel, spaced-apart relation.

The rods 82 and 84 extend beyond the proximal end 14 of the tubular member 12, through the sphere 78 and terminate in a free-wheeling electrical connector 130. The free-wheeling connector 130 cannot move translationally in the handle assembly, but can freely rotate. External leads originating at an electrosurgical generator (not shown) as known in the art, provide a RF potential to the scissors instrument to thereby provide a current path through the rods 82 and 84 and to the electrodes 44 and 46 when those electrodes are bridged by tissue to be coagulated.

Figure 5B:
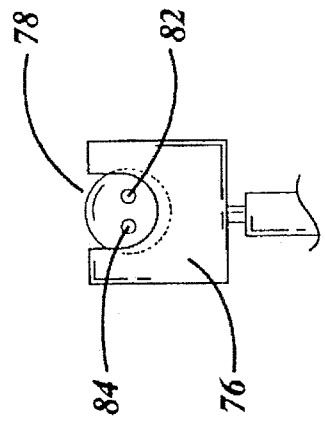
FIG. 5(b) is a front elevation view of a portion of a coupling used in the scissors of FIG. 1 for moving the two moveable blades.
Figure 5A:
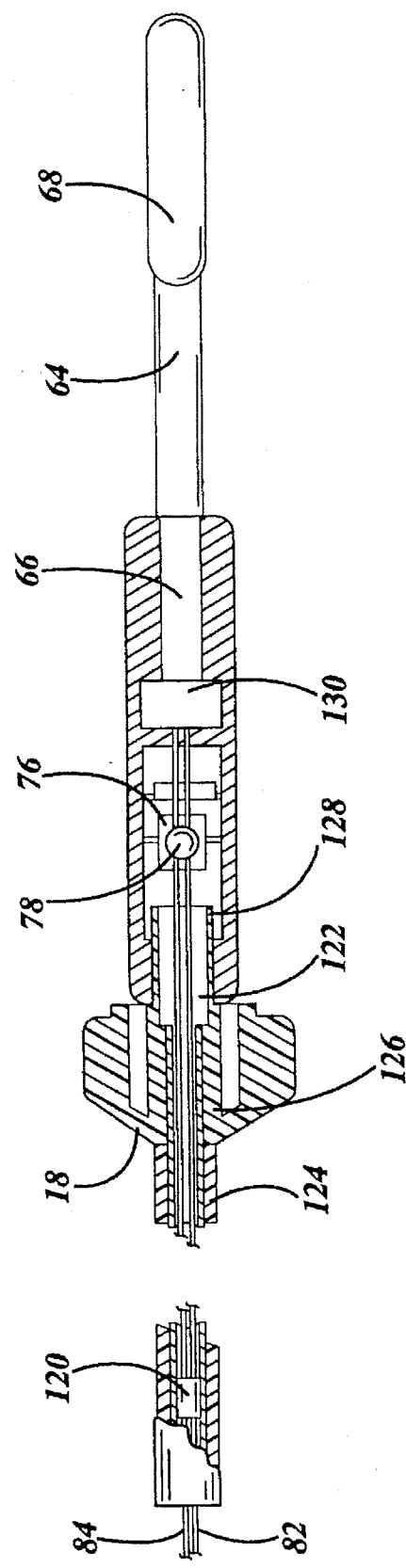
FIG. 5(a) is a partial top plan view of the proximal portion of the scissors of FIG. 1.

The tubular member 12 and the blade assembly 24 can rotatably move because the sphere 78 is freely rotatable within the cradle member 76. The knob 18 is therefore provided near the proximal end 14 of the tubular member 12 to facilitate easy rotation, by hand, of the blade assembly 24 when blade member positioning is performed by the operator. As seen in FIGS. 1 and 5A, the rotatable knob 18 is generally cylindrical in shape, having a bore 122 through its center along a central axis. The bore 122 is large enough to accept a concentrically disposed inner tube 124 therein and to allow the conductive rods 82 and 84 to pass therethrough. The proximal end of the tube 124 is frictionally inserted into the bore 122 to thereby rotate when the knob 18 is rotated. The knob 18 has an integrally formed tubular extension 128. The handle assembly 22 has a complimentary shaped internal contours which accept the extension 128 to thereby allow rotation thereof within the handle assembly 22. The knob 18 is preferably constructed of Nylon® so that the extension 128 will have lubricous characteristics for smoother rotation inside of the handle assembly 22.

Because the push rods 82 and 84 are mechanically connected by the insulating guide member 120 which is stationary within the lumen of the inner tube 124, rotation of the knob 18 results in rotation of the tube 124 as well as of the rods 82 and 84, to thereby also rotate the blade assembly 24. Concurrently, the sphere 78 is rotated in that the rods 82 and 84 both pass through spaced bores in the sphere to their termination in the free-wheeling electrical connector 30. As is evident from FIG. 1, operation of the handle assembly 22 by actuating the movable second handle member 70 relative to the stationary handle 64 moves the cradle member 76 to thereby translationally move the sphere 78 which in turn moves both of the push rods 82 and 84 to thereby pivotally open and close the blade members 26 and 28. In this manner, dual blade movement is accomplished.

An alternative embodiment of the actuation mechanism is shown in FIGS. 6 and 7. The ceramic insulator spacer 120 of FIG. 1 is replaced by a elongated, double lumen tube 140 which is preferably formed from Nylon or another lubricous polymer and which extends through the lumen of the tubular member 142 substantially the entire Length thereof. FIG. 7 shows a cross-sectional view taken through the tubular member 142 and the double lumen tube 140. The push rods 144 and 146 extend individually through the separate lumens and thus remain electrically insulated from one another. In addition to providing this electrical isolation, the double lumen tube 140 also supports the push rods 144 and 146 along substantially their entire length to prevent any bowing thereof when the push rods 144 and 146 are in compression upon actuation of the scissors. As such, the scissors blades 26 and 28 are made to open and close in a more controlled fashion, improving the "feel" of the device.

Although an actuating mechanism having two push rods has been shown, it is to be understood that a mechanism incorporating one push rod, which provides dual pivotal motion of the blades or single pivotal motion of one blade with respect to the other, may be used in place of the dual push rod assembly. In the event one push rod is used, two conductive insulated wires would extend through the lumen to connect the metal traces 44 and 46 comprising the conductive layer to the electrical connector in the handle.

In use, a predetermined RF voltage may be applied across the conductive layers 44 and 46 by way of the conductive rods 82 and 84 and the conductive wires 102 and 104. Because of the presence of insulating layers 40 and 42 coating the blades exterior, the two blades 26 and 28 can touch each other along their entire length as the blades' cutting point moves distally without creating an electrical short circuit therebetween. When it is desired to coagulate the tissue, the RF voltage is applied to the electrosurgical scissors, thereby making the conductive coatings 44 and 46 active bipolar electrodes. When the two blades 26 and 28 are brought into contact with tissue just distal of the cutting point, a current flows from the first electrode 44, through the tissue to the second electrode 46, thereby effecting coagulation. With electrodes 44 and 46 being of substantially equal surface area, tissue is blanched equally on both sides of the blades as cutting progresses.

In the embodiments of the invention described thus far in this specification, electrocoagulation is achieved by applying a RF voltage between a pair of closely spaced electrodes located on the non-shearing surface of cooperating scissors blades. The electrodes are electrically isolated from the blade members themselves by an intermediate layer of insulation. Thus, the fact that the interfacing shearing surfaces of the blades are both metal does not result in a short circuit therebetween. In the alternative embodiment of the invention illustrated in FIGS. 8 and 9, the RF voltage for electrocoagulation is provided between the electrode on the non-shearing surface of the blade and the blade on which it resides. Because the two metal blade members are maintained at the same electrical potential, no current flows between them.

As in the earlier described embodiments, the blade assembly 224 is attached to the distal ends 216 of an elongated metal tube 212 and an electrically conductive push rod 282 extends the length of the tube and is mechanically coupled to a movable handle segment of a scissors-style handle in the same fashion as has already been described. Fitted into the distal end 216 of the tube 212 is a insulating bushing 200 having a bore 202 formed therethrough in which is fitted a metal hub member 208 attached to the distal end of the push rod 282. The hub member 208 is free to slide, within limits, within the bore 202 of the bushing 200.

Each of the blade members 226 and 228 has a shearing surface contacting one another along the lines 227. The non-shearing surface of the blades 226 and 228 are coated with a layer of insulation 240 and 242 and then, on the exterior surface of the insulating layers there are affixed metal electrodes as at 244 and 246.

The blade assembly 224 is affixed to the distal end of the tubular member 212 by way of a metal clevis indicated generally by numeral 248 which includes a pair of parallel, spaced-apart legs 250 and 252. A rivet, as at 254, serves as a clevis pin that passes through aligned apertures formed through the legs 250 and 252 and through similarly aligned apertures formed in the blade members 226 and 228.

To achieve scissors-Like motion to the blade members when the scissors handle is actuated, there is secured to the hub 208 and to the blades 226 and 228 a pair of linkages as at 286 and 288. As in the earlier embodiments, these links are pivotally joined at their respective ends to the blades and to the hub by means of pivot pins. Thus, when the push rod 282 is reciprocated back and forth by manipulation of the scissors handle, the movement of the hub 208 within the bushing 202 causes the blade members to open and close via the links 286 and 288.

In use, one terminal of the electrosurgical generator (not shown) is electrically connected through a suitable connector device plugged into the stationary portion of the handle to the metal tube 212 while the other terminal thereof connects to the conductive push rod 282. The clevis 248 being in electrical contact with the tube 212 and with the conductive electrodes 244 and 246 causes those electrode surfaces to be at the same voltage. In a similar fashion, the push rod 282, the hub 208 and the linkages 286 and 288 apply the same voltage to each of the blade members 226 and 228, such that there is no potential difference between the contacting shearing surfaces of these blades. When the RF generator is activated with the scissors blades contacting tissue to be coagulated, the current flow through the tissue is between the electrodes 244 and 246 and the respective blades 228 and 226 to which the electrodes are affixed.

The embodiments shown in FIGS. 8 and 9 also makes it possible to remove and replace the blade and push rod assembly while retaining the handle mechanism and barrel for reuse. One need only unscrew the bushing 200 from the end of the tubular barrel 212 to release the clevis and allow the blade assembly and push rod to be withdrawn from the distal end of the instrument. Replacement merely involves substituting a new blade assembly and push rod by threading the push rod down the tubular barrel 212, through the spherical coupler 78 and into the free-wheeling connector 130.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself. For example, while an endoscopic scissors has been used in explaining the invention, it is equally applicable to a scissors designed for open surgery. Hence, the scope of the invention is to be determined from the appended claims.

What is claimed is:

1. A bipolar electrosurgical instrument for cutting and coagulating tissue comprising:

(a) first and second metal blades each having a cutting edge and a shearing surface and supporting an insulative layer on a surface other than the cutting edge and shearing surface thereof and an electrically conductive electrode member on the insulative layer;

(b) means for pivotally joining said first and second blades together with their respective shearing surfaces facing one another;

(c) means coupled to at least one of said first and second blades for imparting a scissors-like movement relative to the other of said first and second blades; and (d) means for applying a voltage between the electrode members of said first and second blades.

2. The bipolar electrosurgical instrument as in claim 1 wherein said shearing surfaces of said first and second blades are curved.

3. A bipolar electrosurgical instrument as in claim 1 wherein said insulative layer is a ceramic material.

4. A bipolar electrosurgical instrument as in claim 1 wherein said insulative layer has a thickness in the range of 1–5 mils.

5. The bipolar electrosurgical instrument as in claim 1 wherein said electrode members comprise a conductive coating including metal traces.

6. The bipolar electrosurgical instrument as in claim 5 wherein said conductive coating has a thickness in the range of 1–5 mils.

7. The bipolar electrosurgical instrument for cutting and coagulating tissue comprising, in combination:

(a) an elongated tubular member having a proximal end, a distal end, and a lumen extending therebetween;

(b) first and second blade members, each comprising a metal blade defining a shearing surface and a non-shearing surface, a conductive layer supported by said non-shearing surface, and an intermediate, electrically insulating layer supported by the blade and disposed between said conductive layer and said non-shearing surface;

(c) means for pivotally joining said first and second blade members to the distal end of said elongated tubular member with said shearing surfaces facing one another;

(d) a handle affixed to said proximal end of said tubular member;

(e) means coupled to said handle and extending through said lumen for imparting a scissors-like movement to at least one of said first and second blade members relative to one another; and (f) means extending through said lumen for applying a voltage between said conductive layers of said first and second blade members.

8. The bipolar electrosurgical instrument as in claim 7 wherein said intermediate electrically insulating layer is a ceramic material.

9. The bipolar electrosurgical instrument as in claim 7 wherein said intermediate electrically insulating layer has a thickness in the range of 1–5 mils.

10. The bipolar electrosurgical instrument as in claim 7 wherein said first and second blade members are curved.

11. The bipolar electrosurgical instrument as in claim 7 wherein said layers comprise conductive coatings including metallic traces.

12. The bipolar electrosurgical instrument as in claim 11 wherein said conductive coating has a thickness in the range of 1–5 mils.

* * * * *

Adverse Decision In Interference

Patent No. 5,540,685, David J. Parins, Richard K. Poppe, BIPOLAR ELECTRICAL SCISSORS WITH METAL CUTTING EDGES AND SHEARING SURFACES, Interference No. 104,190, final judgment adverse to the patentees rendered February 16, 2001, as to claims 1-12.

*(Official Gazette July 10, 2001)*

Adverse Decisions In Interference

Patent No. 5,540,685, David J. Parins, Richard K. Poppe, BIPOLAR ELECTRICAL SCISSORS WITH METAL CUTTING EDGES AND SHEARING SURFACES, Interference No. 104,190, final judgment adverse to the patentees rendered February 16, 2001, as to claims 1-12.
*(Official Gazette July 31, 2001)*